(12) United States Patent
Lilie et al.

(10) Patent No.: US 6,437,095 B1
(45) Date of Patent: Aug. 20, 2002

(54) METHOD FOR PRODUCING CHIMERIC POLYPEPTIDES

(75) Inventors: Hauke Lilie; Susanne Richter; Rainer Rudolph, all of Halle; Kay-Gunnar Stubenrauch, Munich, all of (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/625,570

(22) Filed: Jul. 26, 2000

(30) Foreign Application Priority Data

Aug. 2, 1999 (EP) .............................................. 99115022

(51) Int. Cl.⁷ .............................................. C07K 1/107
(52) U.S. Cl. ....................................... 530/345; 530/402
(58) Field of Search .................................. 530/345, 402

(56) References Cited

FOREIGN PATENT DOCUMENTS

| WO | 94/10191 | * | 5/1994 |
| WO | WO 94/29350 | | 12/1994 |
| WO | WO 98/50431 | | 11/1998 |

OTHER PUBLICATIONS

O'Shea, E.K. et al., Current Biology, 3, pp 658–667 (1993).
Zhu, Z. et al., Protein Science, 6, pp 781–788 (1997).
McPhee F. et al, Pro. Nat. Acad. Sci USA, 93, pp 11477–11481 (1996).
Wells J.A. et al, Journal of Biological Chemistry, 261, pp 6564–6570 (1986).
Huston, J.S., et al. (1988) Proc. Natl. Acad. Sci., USA 85, 5879–5883.*
Bird, R.E., et al. (1988) Science 242, 423–426.*
Stemmer, W.P.C., et al. (1993) Biotechniques 14(2), 256–265.*

* cited by examiner

*Primary Examiner*—Charles L. Patterson, Jr.

(57) ABSTRACT

A chimeric polypeptide has a first and a second polypeptide chain chemically linked via 1 to 3 cysteine-based disulfide bridges. The first polypeptide chain consists of 1 to 3 cysteines and 4 to 12 basic amino acids preferably selected from the group consisting of arginine, lysine and ornithine. The second polypeptide chain consists of 1 to 3 cysteines and 4 to 12 acidic amino acids selected from the group consisting of glutamate and aspartate. Each polypeptide chain is linked at its C- or N-terminus to a biologically active compound, and is useful as a multimeric pharmaceutical agent. A method for producing such chimeric polypeptide involves contacting the first polypeptide chain with the second polypeptide chain under conditions such that the basic amino acids on the first polypeptide chain ionically interact with the acidic amino acids on the second polypeptide chain and then treating the first polypeptide chain and the second polypeptide chain with an oxidizing agent under conditions such that the 1 to 3 cysteines of the first polypeptide chain form disulfide bridges with the 1 to 3 cysteines of the second polypeptide chain thereby forming the chimeric polypeptide.

17 Claims, 5 Drawing Sheets

METHOD FOR PRODUCING CHIMERIC POLYPEPTIDES

BACKGROUND OF THE INVENTION

1. Field

The invention relates to chimeric polypeptides that are chemically linked via cysteine-based disulfide bridges (e.g. cystine), methods for producing such polypeptides, and uses thereof.

2. Description

Artificial bifunctional or multifunctional biologically active compounds can be used in diagnostics and therapy, for example immunodiagnostics and immunotherapy. The specific binding of an antibody, or of an antibody fragment, to its antigen can advantageously be used to direct a protein having a different biological function towards the specific antigen. For instance, a bispecific antibody whose antigens are located, on the one hand, on tumor cells, and on the other hand, on macrophages, can be utilized for directing killer cells towards a tumor (Bohlen, H. et al., Blood 82 (1993) 1803–1812). Such bispecific antibodies can be produced by fusing two hybridoma cells that produce the respective monospecific antibodies, to form quadroma cells that may also produce bispecific antibodies (Milstein, C. and Cuello, A. C., Nature 305 (1983) 537–540). Regrettably, this method of obtaining bispecific proteins is limited exclusively to antibodies and only about 15% of those antibodies expressed exhibit the desired bispecificity. Furthermore, these antibodies have to be isolated by labor-intensive purification methods.

Another method of producing bispecific proteins is based on the chemical cross-linking of two proteins having the desired properties (Fanger, M. W. et al., Crit. Rev. Immunol. 12 (1992) 101–24). Cross-linking is accomplished by means of bifunctional linker molecules which react with amino groups of the proteins or with cysteine residues. In the latter case, cysteine residues of the one protein may be activated by 5,5'-dithiobis-(2-nitrobenzoic acid) ("DTNB"). The addition of the second protein which contains cysteine residues in reduced form causes the formation of disulfides, thereby covalently coupling the two proteins. Using this method, the yield of heterodimeric bifunctional proteins can be improved compared to non-specific cross-linking, which usually results in a high proportion of homodimers. Unfortunately, this method still results in non-homogeneous material that may impact negatively on the stability and functionality of the bispecific construct (Debinski, W. and Pastan, I., Bioconjug. Chem. 5 (1994) 40–43).

A common method for producing bifunctional proteins forms a DNA construct that links the 5' end of a cDNA encoding a protein with the 3' end of a gene encoding another protein, while retaining the reading frame. This DNA construct is then expressed recombinantly. In this manner, an antibody fragment directed against a tumor was fused with a bacterial toxin capable of specifically killing tumor cells (Brinkmann, U. et al., Proc. Natl. Acad. Sci. USA 88 (1991) 8616–8620). Fusions of antibody fragments were also successfully produced with RNase and other enzymes, and their functionality was examined in cell cultures (Newton, D. L et al., J. Biol. Chem. 267 (1992) 19572–19578; Zewe, M. et al., Immunotechnol. 3 (1997) 127–136).

Diabodies represent another form of fusion proteins (Holliger, P. et al., Proc. Natl. Acad. Sci. USA 90 (1993) 6444–6448). Diabodies consist of two Fv fragments having different specificities. Unlike scFv fragments in which the two variable domains of an antibody are connected to one another via a linker, in diabodies the VL domain of the one antibody is fused with the VH domain of a second antibody. The structure of the linker used for this purpose prevents intramolecular association of the two domains, and instead causes an intermolecular association of the two constructs, resulting in the formation of a bifunctional diabody.

Numerous attempts have been made to develop systems to produce bifunctional proteins. To this end, proteins were fused at the gene level with peptides or proteins as dimerization domains to impart directed association. As dimerization units were used the antibody domains CL and CHl, calmodulin and the corresponding binding peptide or streptavidine (Müller, K. M. et al., FEBS Lett. 422 (1998) 259–264; Neri, D. et al., BioTechnology 13 (1995) 373–377; Dübel, S et al., J. Immunol. Methods 178 (1995) 201–209). In addition, short peptide sequences such as leucine zippers and amphiphilic helices could also be used as functional units for the directed heterodimerization (Kostelny, S. A. et al., J. Immunol. 148 (1992) 1547–1553). However, to date, no generally applicable method for directed association has been established.

SUMMARY OF THE INVENTION

The subject invention provides a method for producing a chimeric polypeptide having two polypeptide chains that are linked to each other by 1 to 3 cysteine-based disulfide bridges. This method comprises providing a first polypeptide chain and a second polypeptide chain, bringing the first polypeptide chain into spacial proximity with the second polypeptide chain under conditions such that the basic amino acids on the first polypeptide chain interact ionically with the acidic amino acids on the second polypeptide chain, and treating the first polypeptide chain and the second polypeptide chain that have interacted ionically with each other with an oxidizing agent. In this method, the first polypeptide chain consists essentially of from 1 to 3 cysteines and from 4 to 12 basic amino acids selected from the group consisting of arginine, lysine, and ornithine. The first polypeptide has attached to its C- or N-terminus a first biologically active compound. The second polypeptide chain consists essentially of 1 to 3 cysteines and 4 to 12 acidic amino acids selected from the group consisting of glutamate and aspartate. The second polypeptide has attached to its C- or N-terminus a second biologically active compound.

With respect to the treating the first polypeptide chain and the second polypeptide chain that have interacted ionically with each other with an oxidizing agent, such oxidation is under conditions such that the 1 to 3 cysteines of the the first polypeptide chain form disulfide bridges with the 1 to 3 cysteines of the second polypeptide chain and thus produce the chimeric polypeptide. This chimeric polypeptide can then be isolated.

It is preferred that the first polypeptide chain and the second polypeptide chain each have 2 or 3 cysteines. The distance between any two cysteines in a polypeptide chain is preferably more than one amino acid, for example, from 3 to 6 amino acids.

BRIEF DESCRIPTION OF THE FIGURES

FIG. 5: Elution profile of the association reaction of FabD10SCP and α-glucosidase R10CGP at low ionic strength (TosoHaas TSK 2000 SWXL; 50 mM $Na_2HPO_4$/ $NaH_2PO_4$ pH 7.0; 300 mM NaCl; flow rate 0.75 ml/min; column volume: 14.335 ml). The results of the bifunctionality assay (modified ELISA) that detect only molecules containing both the Fab and the α-glucosidase are shown. 100 μl aliquots of the eluted fractions were incubated with 1 ml of biotinylated creatine kinase solution (5% blocking reagents) in streptavidin coated tubes for 1 h at room temperature; after washing twice with high salt buffer (2 M NaCl; 10 mM Tris-HCl pH 7.5) and once with low salt buffer (10 mM Tris-HCl pH 7.5); the tubes were incubated with 800 μl 2 mM para-nitroglucopyranoside in 100 mM $K_2HPO_4$/$KH_2PO_4$ pH 6.8 at 30° C. for 3 h; the absorbance was measured at a wavelength of 405 nm against a reference. The high molecular weight fraction containing the chimeric protein shows highest bifunctional activity. The presence of non-associated α-glucosidase results in low background signal.

DETAILED DESCRIPTION OF THE PREFERRED EMBODIMENTS

The invention will now be described in terms of its preferred embodiments. These embodiments are set forth to aid in understanding the invention but are not limiting.

Preferably, the invention comprises a chimeric polypeptide consisting of a first and a second polypeptide chain that are chemically linked via 1 to 3 cysteine-based disulfide bridges. The first polypeptide chain consists of 1 to 3 cysteines and 4 to 12 basic amino acids, preferably selected from the group consisting of arginine, lysine and ornithine, and the second polypeptide chain consists of 1 to 3 cysteines and 4 to 12 acidic amino acids, preferably selected from the group consisting of glutamate and aspartate. Each of the polypeptide chains is linked at its C- and/or N-terminus to a biologically active compound.

In a preferred embodiment of the invention, the biologically active compounds differ from each other by their chemical structure. For example, it is preferred that the compound is an antibody, antibody fragment, or enzyme.

The invention also provides a method for the production of a chimeric polypeptide that is chemically linked via 1 to 3 cysteine-based disulfide bridges and consists of a first and a second polypeptide chain. The first polypeptide chain consists of 1 to 3 cysteines and 4 to 12 basic amino acids, preferably selected from the group consisting of arginine, lysine and ornithine, and the second polypeptide chain consists of 1 to 3 cysteines and 4 to 12 acidic amino acids, preferably selected from the group consisting of glutamate and aspartate. Each of the polypeptide chains is fused at its C- and/or N-terminus to a biologically active compound. The two nucleic acids encoding the two polypeptide chains, which are each linked to a biologically active polypeptide, are expressed in a prokaryotic or eukaryotic host cell simultaneously or separately and are recovered from the host cell or the supernatant. The polypeptides are then treated with an oxidizing agent to form disulfide bridges and the chimeric polypeptide is isolated.

The subject method preferrably produces chimeric polypeptides that essentially avoid the formation of homodimers, if heterodimers are the desired products.

A polypeptide chain consisting of 4 to 12 basic amino acids specifically interacts in an aqueous solution at low ionic strength with a polypeptide chain consisting of 4 to 12 acidic amino acids. If both polypeptides additionally contain cysteines, in a subsequent reaction, disulfide bridges can be specifically formed between the cysteines of both polypeptide chains under oxidizing, or even slightly reducing, conditions. Preferably, the distance between two cysteines in the polypeptide chain is more than one amino acid, preferably 3 to 6 amino acids. This implies that the amount and distance of the cysteines of both polypeptides are preferably identical and that if the cysteines of both polypeptides are positioned opposite each other, then acidic amino acids of the one strand and the basic amino acids of the other strand are in each case also positioned opposite. Identical distance of the cysteines means that in both strands the same amount of amino acids other than cysteine is positioned between the cysteines.

According to the invention, it is possible to link two or more biologically active compounds together via the first and second polypeptide chains in a stable and covalent form and in a spatially defined position.

In a further preferred embodiment of the invention, the first and second polypeptide chains are designed to position the cysteines and the basic and acidic amino acids to enable an optimized ionic interaction between the acidic and basic amino acids and coupling via one or more disulfide bridges, in a preselected directed form. In this way it is possible to bring the biologically active compounds into a preselected spatial position with respect to one another. For example, when the first and second polypeptide chains are in a position where their N-terminal ends meet and where their C-terminal ends meet, the biologically active compounds can be brought into a very close spatial position relative to one another, if they are both linked at the C-terminus (or are both linked at the N-terminus) of the polypeptide chains. If one of the biologically active compounds is linked at the C-terminus and the other is linked at the N-terminus of the polypeptide chains, their spatial distance from one another is much greater. In such case, the dimerized first and second polypeptide chains essentially act as a linear linker between two biologically active compounds, preferably between two polypeptides. An analogous procedure can be adopted when four biologically active compounds are to be brought into a spatial position relative to one another.

As used herein, "chimeric polypeptide" means a polypeptide that consists of a first and a second polypeptide chain. The first and second polypeptide chain differ from each other chemically and are composed in such a way that they bind to one another as a result of ionic interaction via a plurality of amino acids carrying different charges and are additionally covalently bound to one another via disulfide bridges of cysteines. In producing the chimeric polypeptides, the polyionic interactions between the acidic and basic amino acids in the polypeptide chains serve to bring the polypeptides into a preselected position relative to one another, which position makes it possible to easily form the disulfide bridges. The chimeric polypeptides can couple the biologically active compounds to one another in a stable and predefined manner, avoiding undesired byproducts (e.g., homodimers, or chimeric products where the biologically active compounds are in an unfavorable position relative to one another). Usually, the first and second polypeptide chains per se exhibit no substantial biological activity. They are merely auxiliary agents assisting in the coupling of the biologically active compounds, which, in their dimeric or multimeric form, are able to develop a preselected pharmaceutical effect. For a strong ionic interaction between the polypeptide chains it is preferred that the $pK_a$ values of the basic and acidic amino acids, which are positioned on the chains in a position opposite to one another, should differ as much as possible. It is preferred that the $pK_a$-value of the basic amino acid is about 10 or more and the $pK_a$-value of the acidic amino acid is about 4.5 or less.

The polypeptide chains consist two chains each having 1 to 3 cysteines and 4 to 12 additional amino acids. For the first polypeptide chain, the amino acids are preferably selected from the group consisting of arginine, lysine and ornithine. For the second polypeptide chain, the amino acids are preferably selected from the group consisting of glutamate and aspartate. In a preferred embodiment, the polypeptide chain consists of 6 to 10 basic or acidic amino acids. It is further preferred that the polypeptide chains each contain a cysteine residue. However, also other acidic or basic amino acids or derivatives thereof can be used according to the invention as long as their $pK_a$-values differ considerably (preferred difference about 5 or more units) and ionic interaction leads to binding of the two polypeptide chains.

Any desired biologically active compound can be used as the biologically active compound.

The term "biologically active compound or material" as used herein therefore refers to an organic molecule that causes a biological effect when administered in vivo to an animal. An organic molecule can include a drug, a biological macromolecule such as a peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or a combination thereof. An animal can include birds and mammals, such as humans.

The term "drug" as used herein refers to any substance used internally or externally as a medicine for the treatment, cure or prevention of a disease or disorder. Examples of a drug include immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, and radiation absorbers, such as UV-absorbers.

The term "biologically active agent" includes agents such as insecticides, pesticides, fungicides, rodenticides, and plant nutrients and growth promoters.

Biological macromolecules, preferably having a molecular weight in the range of two or three thousand to many millions, are important regulators of physiological functions. The size and tertiary structure of a biologically active macromolecule convey significant chemical information through highly specific interactions with receptors, enzymes, nucleic acids or other biological mediators interacting with it. Events as diverse as thrombosis, inflammation and immunologic responses are controlled, at least in part, by the three-dimensional topology of macromolecules. The surface of the macromolecule is composed of geometrically distributed groups which impart ionic, hydrophobic, steric, electrostatic and hydrogen bonding character to the molecule and provide the molecular template for receptor binding.

Acid mucopolysaccharides, also referred to as glycosaminoglycans ("GAG"), consist of recurring disaccharide units, each of which contains a derivative of an aminohexose, usually D-glucosamine or D-galactosamine. At least one of the two sugars in the recurring disaccharide unit of acid mucopolysaccharides contains an acidic group having a negative charge at pH 7, either a carboxylate or a sulfate group. An important acid mucopolysaccharide is heparin, which is generated by certain types of cells that are abundant in the lining of arterial blood vessels. Heparin inhibits blood clotting and aids in preventing the formation of blood clots in circulating blood (Jackson, R. L., et al., Physiol. Reviews 71 (1991) 481–522).

It is known that GAG is a mediator of cellular processes (angiogenesis, nerve cell development, smooth muscle cell proliferation), gene expression and homeostasis. GAG interacts with DNA (Davidson, J. N., in "The biochemistry of the nucleic acids" Methuem, London, 1969).

Both DNA and GAG are linear polymers that have polyanionic charges that are essential for biological activity. The rigidity of the DNA helix insures that the specifically sequenced nucleic acids are presented so as to obtain a desired biological interaction.

Proteins are the most abundant macromolecules in cells, making up over half their dry weight. Proteins and peptides are known to carry chemical information in their tertiary structures. A number of proteins occurring in nature are conjugated to other chemical groups. Examples are lipoproteins, glycoproteins, phosphorproteins, hemoproteins, flavoproteins and metalloproteins.

Proteins have diverse biological functions. Nonlimiting examples are transport proteins (for example, hemoglobin and serum albumin), nutrient and storage proteins (for example, gliadin, ovalbumin, casein, and ferritin); contractile or motile proteins (for example, actin, myosin, tubulin, and dynein); structural proteins (for example, keratin, fibroin, collagen, elastin, and proteoglycans); defense proteins (for example, antibodies, immunoglobulins, fibrinogen, thrombin, botulinus toxin, diphtheria toxin, snake venom, and ricin); enzymes; and regulatory proteins (for example, insulin, growth hormone, corticotropin and repressors).

Hormones are classified as peptide hormones such as thyrotropin-releasing factor, corticotropin, vasopressin, insulin, and glucagon; amine hormones such as adrenaline and thyroxine; or steroid hormones such as cortisol, β-estradiol, testosterone, and progesterone. Other hormones include adrenocorticotropin-releasing hormone, somatotropin releasing hormone, somatostatin, prolactin-releasing hormone, prolactin-inhibitory hormone, FSH- and LH-releasing hormone, vasopressin, and oxytocin.

Therapeutic biologically active compounds may also be selected from the general group consisting of anti-neoplastic agents, anti-infective agents, anti-depressives, antiviral agents, anti-nociceptive agents, anxiolytics, and hormones.

Representative examples of anti-neoplastic agents useful in the compositions and methods of the present invention include methotrexate, taxol, tumor necrosis factor, chlorambucil, interleukins, bleomycin, etoposide, fluorouracil, and vinblastine.

Representative examples of anti-infective agents useful in the compositions and methods of the present invention include pentamidine, metronidazole, penicillin, cephalexin, tetracycline, and chloramphenicol.

Representative examples of anti-viral agents useful in the compositions and methods of the present invention include dideoxyoytidine, zidovudine, acyclovir, interferons, dideoxyinosine, and ganciclovir.

Representative examples of anxiolytics and sedatives useful in the compositions and methods of the present invention include benzodiazepines such as diazepam, barbiturates such as phenobarbital, and other compounds such as buspirone and haloperidol.

Representative examples of hormones useful in the compositions and methods of the present invention include estradiol, prednisone, insulin, growth hormone, erythropoietin, and prostaglandins.

Representative examples of anti-depressives useful in the compositions and methods of the present invention include fluoxetine, trazodone, imipramine, and doxepin.

Representative examples of anti-nociceptives useful in the compositions and methods of the present invention include hydromorphine, oxycodone, fentanyl, morphine, and meperidine.

The therapeutic biologically active compounds described above are exemplary and not meant to limit the scope of the present invention in any fashion. Many other classes of pharmacologic compounds would be useful in the compositions and methods of the present invention, including local anesthetics, vitamins, vaccines, wound healing stimulators, immunosuppressives, anti-emetics, anti-malarial agents, anti-fungal agents, anti-psychotics, anti-pyretics, coagulants, diuretics, calcium channel blockers, bronchodilatory agents, etc.

Biologically active compounds can be linked to the polypeptide chains using methods known in the art, for example by chemical coupling via reactive groups, such as amino or carboxyl groups. For example, such methods are described in Mattson et al., Mol. Biol. Rep. 17 (1993) 167–183.

If the biologically active compound is a polypeptide, it is also possible to construct the nucleic acid that contains both the sequence of one of the first and second polypeptide chain and the sequence of one or more polypeptides which are the biologically active compounds, express them by recombinant means in prokaryontic or eucaryontic host cells, recover the recombinant polypeptides and link them together according to the invention.

It is particularly preferred to construct chimeric polypeptides wherein the biologically active compounds are two different antibodies or antibody fragments (Fab, Fc, Fv fragments) or wherein one biologically active compound is an antibody or an antibody fragment and the other is a polypeptide having enzymatic activity like kinases, phosphatases, RNases, toxins or specific binding activities such as transcription factors.

It is further preferred to use as a first biologically active compound a substance which specifically binds to cell surfaces whereas the other biologically active compound is a pharmaceutically active compound which is to develop its therapeutic effect at this site. In this connection, for example, the first biologically active compound is a ligand for a cell surface molecule such as, CD40 or CD40L (CD154) and a second biologically active compound is a pharmaceutically active compound such as an anti-sense nucleic acid or a cytostatic compound.

Other examples of therapeutic include using a tumor specific antibody as first biological active compound and pseudomonas exotoxin, diphtheria toxin, transcription factors activating p53 production or other apoptosis inducing factors, as the second biological active compound.

Another combination of biological active compounds could be the association of gp120-HIV binding domain of CD4 and any antiviral or cytotoxic drug capable of blocking viral maturation or killing the infected cell.

Not only bifunctional but multifunctional oligomers could be created by the invention using as one compound (not necessarily biologically active) a multivalent system, allowing the covalent association via polyionic interactions and a disulfide bridge of different biological active compounds. For example, a virus shell displaying several polyionic peptide sequences on the surface could provide such a multivalent matrix.

According to the invention, nucleic acids encoding two polypeptide chains each linked to a biologically active polypeptide are expressed in a prokaryotic or eukaryotic host cell simultaneously or separately. The polypeptides are recovered from the host cell or the supernatant, treated with an oxidizing agent to form disulfide bridges, and the chimeric polypeptide is isolated. Such "naturation methods" are described, for example, in U.S. Pat. No. 4,933,434, pages 453, 363, and U.S. Pat. No. 5,593,865.

According to the invention, in the first step, the first and second polypeptide chains are coupled via ionic interaction at a neutral or weak basic pH (preferably pH 7 to 8.5) and at low ionic strength (preferably 0 to 200 mmol/l NaCl). In the second step, the polypeptide chains are either directly covalently linked via the disulfide bridge, whereby a mixed disulfide is formed and the two polypeptide chains are linked together via disulfide bridging under oxidizing or weakly reducing conditions. In a preferred embodiment of the invention, GSH is used in combination with GSSG whereby the ratio GSH:GSSG is from 5:1 to 1:5, at a neutral or weak basic pH value.

EXAMPLES

The following examples, references, sequence listing and figures are provided to aid the understanding of the present invention, the true scope of which is set forth in the appended claims. It is understood that modifications can be made in the procedures set forth without departing from the spirit of the invention. The invention is only to be limited by the claims that follow and their equivalents.

Example 1

Specific Association and Covalent Linkage of Polyionic Peptides a) Association and Linkage The specific association and covalent linkage of peptides via polyionic interactions and a disulfide bond was analyzed using the polyionic peptides (SEQ ID NO:1) AlaCysGluGluGluGluGluGluGluGlu ($ACE_8$) and (SEQ ID NO:2) Ala- CysLysLysLysLysLysLysLys (ACK$_8$). All peptides were synthesized on an ABI Applied Biosystem peptide synthesizer 431A according to the Fmoc method. 1 mM peptide was dissolved in 20 mM sodium borate pH 8.5, 2 mM EDTA (concentration checked according to Ellman, G. L., Arch. Biochem. Biophys. 82 (1959) 70–77).

Formation of disulfide bonded heterodimers was analyzed by cation exchange chromatography. Samples were loaded on a POROs 20 HS column (column volume 1.7 ml, equilibrated in 50 mM sodium phosphate pH 7.0). Elution was performed with a linear gradient of NaCl between 0 and 2 M at a flow rate of 4 ml/min. The peptide ACK8 eluted at 1070 mM NaCl, the mixed disulfide of ACK8 and glutathione (ACK8-SG) at 800 mM NaCl and the disulfide bonded heterodimer ACK8-ACE8 at 350 mM NaCl. ACE8 did not bind to the column. The amount of peptides was quantified by integrating the peak areas of the absorbtion at 205 nm (Pharmacia Unikorn software).

The specificity of association of the peptides ACK8 and ACE8 was measured in dependence on different parameters:
b) influence of ionic strength
c) significance of the redox potential for formation the disulfide bond between the peptides
d) competition of association using uncharged, cysteine containing peptides and proteins b) Influence of Ionic Strength (NaCl Concentration) on Disulfide Bond Formation Between ACE8 and ACK8

200 µM ACK8 was converted to the mixed disulfide form ACK8-SG using 10 mM GSSG in a buffer 500 mM sodium borate pH 8.5. This mixed disulfide was purified by ion exchange chromatography. The specific association and redox reaction of 20 µM ACE8 and the mixed disulfide ACK8-SG was carried out in 20 mM sodium borate pH 8.5, 2 mM EDTA, 25° C. in the presence of NaCl at concentration between 0 and 1 M. After an incubation of 30 min further redox reaction was blocked by adding 20 mM iodoacetamide. Analyses of formation of heterodimers were performed by cation exchange chromatography as described before.

Figure 1:
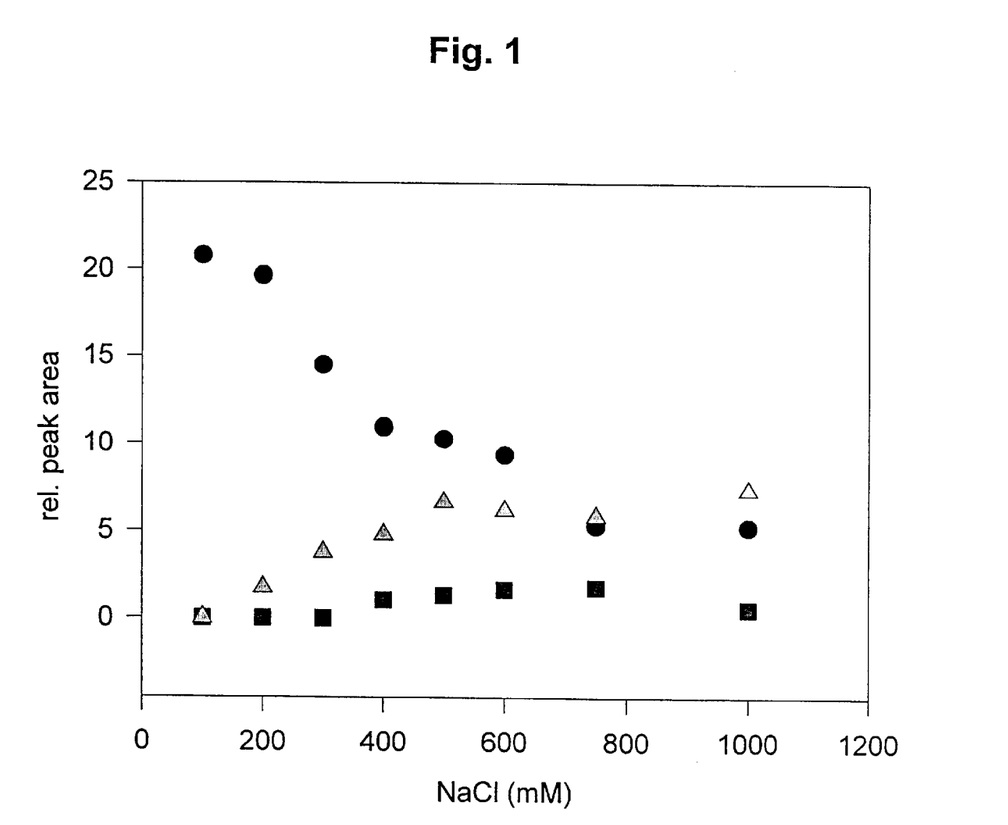
FIG. 1: Formation of the disulfide bonded heterodimer ACE8-ACK8 in dependence on the NaCl concentration in the buffer. The relative amounts of ACK8 (▲), the mixed disulfide between ACK8 and GSSG (ACK8-SG, ■) and the disulfide linked heterodimer ACE8-ACK8 (●) are shown.

The disulfide bonded heterodimer ACK8-ACE8 was quantitatively formed at NaCl concentrations below 200 mM. At higher salt concentrations the polyionic interaction between the peptides was suppressed, leading to lower yields of heterodimer formation.

c) Dependence of Disulfide Bonding Between ACE8 and ACK8 on the Redox Potential

50 µM ACK8 and 75 µM ACE8 were incubated in 100 mM sodium phosphate pH 8.5, 2 mM EDTA at 25° C. in the presence of 2.5 mM redox substances (GSH and GSSG). The redox potential of the buffer was varied by changing the ratio of GSH and GSSG. After 5 h incubation the reaction was stopped by adding 100 mM iodoacetamide and analyzed as described before.

Figure 2:
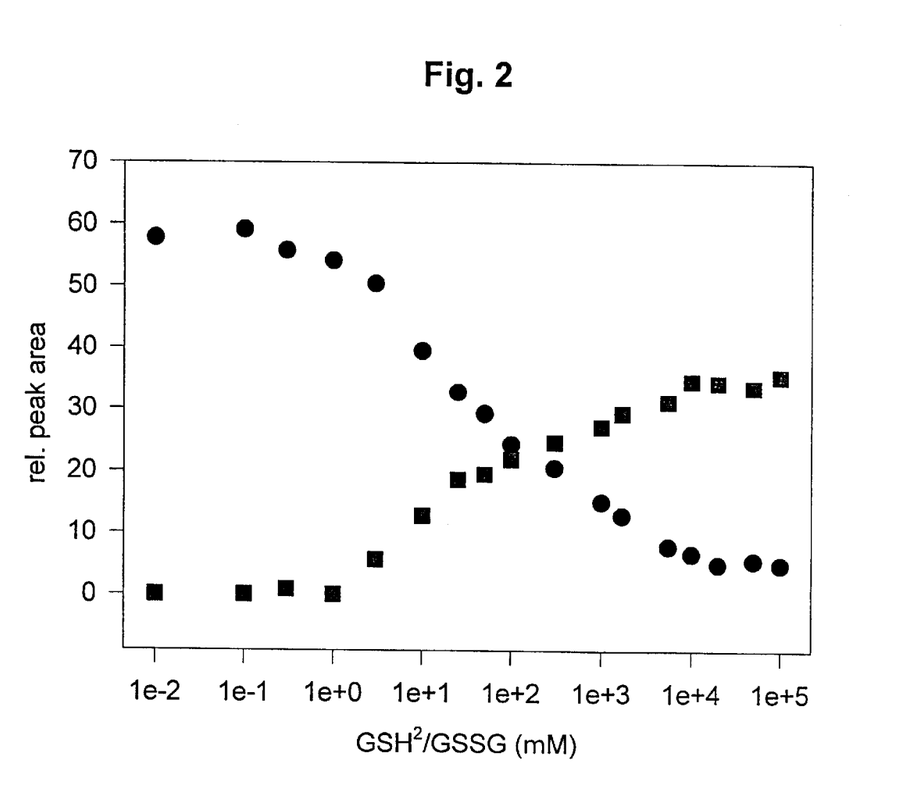
FIG. 2: Formation of the disulfide bonded heterodimer ACE8-ACK8 in dependence on the redox potential of the buffer. The amount of heterodimer ACE8-ACK8 (●) and the non-converted peptide ACK8 (■) are given.

Specific association and covalent linkage of the peptides ACE8 and ACK8 occurred even under reducing conditions. The formation of the heterodimer ACE8-ACK8 was quantitative at redox conditions of $GSH^2/GSSG=1:1$ (mM).

d) Competition of Disulfide Bond Formation Between ACK8 and ACE8

The specificity of disulfide bond formation between ACE8 and ACK8 was analyzed using a competition approach. 25 µM ACK8 and 37.5 µM ACE8 were incubated in 100 mM sodium borate pH 8.5, 2 mM EDTA, 0.5 mM GSH, 2 mM GSSG in the presence of 250 µM of laminin nona-peptide (sequence: CysAspProGlyTyrIleGlySerArg, SEQ ID NO:3). In another experiment the redox potential of the buffer was created by 1.65 mM GSH and 0.85 mM GSSG. As a control the same experiments in the absence of the laminin peptide were performed. After 2 h incubation the reaction was blocked by acidification (pH 2) and the products analyzed by RP-HPLC. The amount of heterodimeric ACE8-ACK8 in the controls was set to 100% and the yield of heterodimer formation in the competition experiments analyzed.

As a second competitor α-glucosidase (68.1 kDa) was used. This protein contains 5 cysteines, accessible for low molecular weight thiol reagents. 25 µM ACK8 and 37.5 µM ACE8 were incubated in sodium borate pH 8.5, 2 mM EDTA in the presence of 60 µM α-glucosidase. The two different redox conditions were identical to those described before. Analyses were performed by RP-HPLC.

Figure 3:
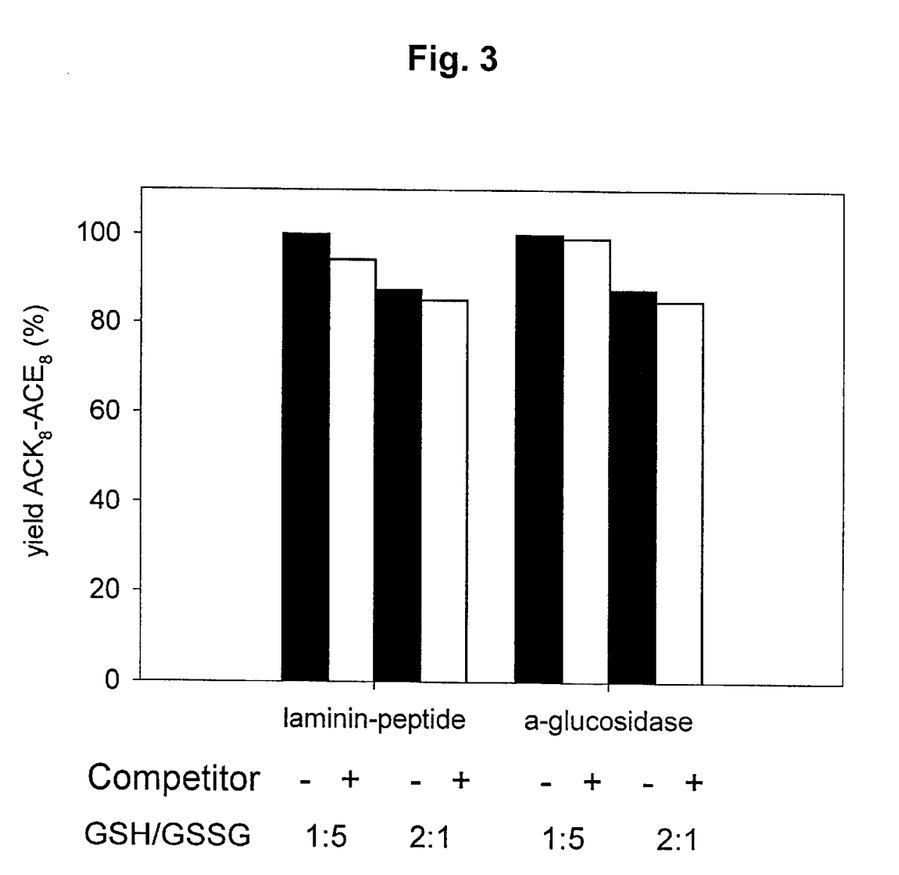
FIG. 3: Formation of the disulfide bonded heterodimer ACE8-ACK8 in dependence on a tenfold molar excess of a cysteine containing laminin peptide and α-glucosidase is analyzed, respectively. The competition is performed in buffers with two different redox systems.

The formation of heterodimeric and covalent linked ACE8-ACK8 was not influenced by the addition of an excess of laminin peptide and α-glucosidase, respectively. Based on the polyionic interactions between ACE8 and ACK8 the dimerisation of these peptides to ACE8-ACK8 is highly specific.

Example 2

Formation of a Chimeric Oligomer Consisting of a Fab-fragment and α-glucosidase From *Saccharomyces Cerevisiae* Using Polyionic Fusion Peptides The antigen binding activity of the Fab-fragment of MAb33 is combined with the enzymatic activity of α-glucosidase using polyionic fusion peptides leading to the formation of a bifunctional antibody derivative (chimeric polypeptide).

The Fab fragment of MAb 33 was modified genetically so that it contains a negatively charged fusionpeptide with an additionally cysteine residue at its C-terminus: AspAspAspAspAspAspAspAspAspAspSerCysPro (abbreviated as $D_{10}SCP$, SEQ ID NO:4). The second polypeptide chain is a derivative of α-glucosidase PI from *Saccharomyces cerevisiae* carrying a positively charged C-terminal fusion peptide (ArgArgArgArgArgArgArgArgArgArgCysGlyPro (abbreviated as $R_{10}CGP$, SEQ ID NO:5).

The formation of the chimeric protein includes the following steps:
I. Production of a Fab-fragment With a C-terminal Polyionic Fusion Peptide
a) Construction of the expression vectors
b) Expression in *E. coli*, isolation of inclusion bodies, solubilisation and renaturation
c) Purification by anion exchange chromatography
II. Production of α-glucosidase With a C-terminal Polyionic Fusion Peptide
a) Construction of the expression vector
b) Expression in *E. coli* in soluble form
c) Purification by ion exchange chromatography
III. Formation of a Disulfide Linked Chimeric Protein Mediated By Polyionic Fusion Peptides
I. Production of a Fab-fragment With a C-terminal Polyionic Fusion Peptide
a) Construction of the Expression Vectors Fab fragment of mAb (monoclonal antibody) 33 was used as one part of the chimeric protein. MAb 33 is a murine antibody of subclass kIgG1 directed against the dimeric muscle-specific human creatine kinase (CK-MM E. C. 2.7.3.2.) (Buckel et al., Gene 51 (1987) 13). The Fab fragment of mAb 33 contains a disulfide bond between the light chain k (25 kD) and the heavy chain fd (25 kD).
a1) Construction of a Plasmid Encoding the Light Chain (Kappa)

The light chain of mAb 33 was encoded on plasmid pBT111 which is a derivative of the plasmid pBR223-3. The sequence and cloning strategy is described in EP 0 364 926 B1. For expression the plasmid was transformed into *E.coli* host cells containing the plasmid pUBS520 (Brinkmann et al., Gene 85 (1989) 109–114).

a2) Construction of Plasmids Encoding a Fusion Protein of the Heavy Chain With a C-terminal Polyionic Peptide Sequence Vector construction started with a plasmid p12016 encoding the heavy chain of mAb 33 (Buckel et al., Gene 51 (1987) 13). The nucleotide sequences encoding the Ch2 and Ch3 domains of the heavy chain were deleted and a nucleotide sequence coding a polyionic peptide with a cysteine at its C-terminus was added at the ch1 domain using primer mutagenesis. The nucleotide sequence contains auxiliary codons at its 5'-terminus encoding the five N-terminal amino acid residues of β-galactosidase (ITNSR) in order to facilitate protein expression in *E. coli*. The cDNA encoding the fd-fragment was amplified with the primers 1 and 2 by PCR. At the 5'-terminus a NdeI restriction site was inserted. At the 3'-terminus a Hind III restriction site and the nucleotide sequence of the polyionic peptide with the additional cysteine were inserted.

The PCR was carried out with the following primers:
Forward primer: N-terminal NdeI Fd (SEQ ID NO:6):
   5'-GCG TTA GCC ATA TGA CCA TGA TTA CGA ATT CCC GG-3'
Reverse primer of the $fdD_{10}SCP$-variant (SEQ ID NO: 7):
   5'-CAT AGT CCC AAG CTT TTA CGG GCA AGA ATC ATC GTC ATC ATC ATC GTC GTC ATC ATC ACC ACA ATC CCT GGG CAC AAT-3'

The modified cDNA-fragment was cloned into the vector pET-11a (Novagen) which belongs to the T7-expression systems (Studier, F. W., and Moffatt, B. A., J. Mol. Biol. 189 (1986) 113). For expression the vector was transformed into host cells containing plasmid pUBS520. The plasmid pUBS520 (Brinkmann et al., Gene 85 (1989) 109–114) encodes a tRNA which is necessary for translation of the codons AGA and AGG rarely occurring in *E. coli*.

b) Expression in *E. coli*, Isolation of Inclusion Bodies, Solubilisation and Renaturation Cultivations were performed on mineral salt medium with glucose as the sole carbon source at 37° C. at a scale of 5-liters in a fermenter. Four hours after induction with 0.4 mM IPTG the cells were harvested by centrifugation (5000 rpm; 20 min; 4° C.). The biomass was stored at −70° C. The overexpressed recombinant protein accumulated in inclusion bodies in the bacterial cytosol. The inclusion bodies were isolated according to Rudolph et al., Folding Proteins, In: T. E. Creighton (ed.): Protein function: A Practical Approach, 57 (1996) and stored at −20° C. The protein aggregates were solubilized in 6 M guanidine hydrochloride (100 mM TRIS-HCL pH 8.5; 1 mM EDTA; 100 mM DTT) at 4° C. overnight. The pH was reduced to 4.0 using 0.5 M HCl and unsolubilized material was separated by centrifugation (20,000 rpm; 30 min; 4° C.). The solution was extensively dialysed against 4 M guanidine hydrochloride pH 4.0 in order to remove dithiothreitol. The protein concentration was determined spectrophotometrically using authentic denatured, reduced Fab fragment as a standard.

The denatured protein was diluted 100-fold in renaturation buffer (1 M Tris/HCl pH 8.0; 2 mM EDTA; 2.4 mM GSSG/0.6 mM GSH) to a final protein concentration of 10 μg/ml. Renaturation was performed at a scale of 10 liters over 150 h at 15° C. The functionality of the renatured Fab fragments was assayed by ELISA according to Buchner, J., and Rudolph, R., Bio/Technology 9 (1991) 157. The renatured protein solution was centrifuged (13,000 rpm; 30 min; 4° C.) in order to remove higher molecular aggregates and the supernatant was concentrated by cross flow filtration (tangential flow ultrafiltration; ProVario-3-System; filter cassette: Minisette OMEGA FSQ; cut off: 8 kD). The retentate of the Fab fragment with the polyaspartate fusion peptide (abbreviated as $FabD_{10}SCP$) was dialysed against 20 mM Tris/HCl pH 8.0.

c) Purification By Anion Exchange Chromatography

The Fab fragment $FabD_{10}SCP$ was purified by anion exchange chromatography using a Resource Q column (Pharmacia; column volume: 6 ml). Elution was performed in a linear sodium chloride gradient from 0 to 1 M in 20 mM Tris-HCl pH 8.0 over 20 column volumes at a flow rate of 6 ml/min. $FabD_{10}SCP$ eluted at a NaCl concentration of 300 mM. The dimer was effectively separated from higher molecular, disulfide bridged $fdD_{10}SCP$-chains which eluted at a sodium chloride concentration of 400 mM.

II. Production of α-glucosidase With a C-terminal Polyionic Peptide Sequence

Wildtype α-glucosidase from *Saccharomyces cerevisiae* is a monomeric protein with a molecular weight of 68 kDa. It contains five cysteines which are not involved in disulfide bonds. In the present investigations a fusion protein was genetically constructed consisting of α-glucosidase PI and a C-terminal deca-arginine fusion peptide with an additional cysteine, glycine and proline.

a) Construction of the Expression Vector

The vector pKK177-3/GlucPI described by Kopetzki et al., Mol. Gen. Genet. 216 (1989) 149, encodes the α-glucosidase PI of *Saccharomyces cereviseae*. The expression vector is a derivative of pKK223-3 (Brosius, J., and Holy, A., Proc. Natl. Acad. Sci. USA 81 (1984) 6929) which contains a tac-promotor and a β-lactamase gene. The vector was modified so that it contains a single EcoRI restriction site at position 1600 of the α-glucosidase gene. The fusion peptide encoding ten arginine residues, a cysteine, a glycine and a proline residue was inserted at the C-terminus by primer mutagenesis using standard recombinant DNA techniques. The PCR was performed using the following primer sequences:

Forward primer EcoRI1600: (SEQ ID NO:8)
   5'-CAT AAG AGT ACG GAG ACA AGA CGC TGT TTG C-3'
Reverse primer R10CGP: (SEQ ID NO:9)
   5'-AAA CAG AAG CTT ATT ATG GTC CAC ATC GAC GTC GAC GAC GCC GGC GAC GTC GGC GTT TGA CCA GGT AGA TTC TAC C-3'

After the digestion of the vector and the PCR products with EcoRI and Hind III they were ligated.

b) Expression in *E. coli* in Soluble Form

For expression the vector was transformed into *E. coli* C600 (Appleyard, R. K., Genetics 39 (1954) 440) pFDX500 ($LacI^q$ in pACYC177 (Chang, A. C. Y., and Cohen, S. N., J. Bacteriol. 134 (1978) 1141). Cultivation and induction was performed according to Kopetzki et al., Mol. Gen. Genet. 216 (1989) 149. the cells were incubated on Luria Broth (LB)-medium supplemented with 2% glucose at 37° C. For induction the pH was reduced from 7.0 to 5.0 with phosphoric acid (3 M) and the temperature was reduced to 24° C. In combination with the limited induction in the presence of 0.5% lactose α-glucosidase predominantly accumulated in soluble form in the cytosol. Six hours after induction cells were harvested by centrifugation (5000 rpm; 4° C.; 10 min) and washed in 10 mM $K_2HPO_4/KH_2PO_4$ pH 6.8; 10 mM EDTA. The biomass was stored at −20° C.

10 g biomass was resuspended in 50 ml buffer (10 mM $K_2HPO_4/KH_2PO_4$ pH 6.8; 10 mM EDTA). The cells were disintegrated by high pressure homogenisation (Gaulin MicronLab 40; 1200 bar; 2 passages). Afterwards the crude extract was incubated in the presence of 15 mM MgCl$_2$ and 1 U/ml Benzonase (Merck, Darmstadt) at 4° C. for two hours. Insoluble cell debris was removed by centrifugation (20,000 rpm; 4° C.; 2 h).

c) Purification By Cation Exchange Chromatography

The supernatant of the crude extract was purified by cation exchange chromatography on a Resource S column (Pharmacia; 6 ml). Protein fraction containing α-gucosidase activity eluted at a NaCl concentration of 350 mM in a linear gradient of 0 to 500 mM NaCl (buffer: 10 mM K$_2$HPO$_4$/KH$_2$PO$_4$ pH 6.8; 10 mM EDTA) over 20 column volumes at a flow rate of 6 ml/min. Enzymatic activity was determined spectrophotometrically according to Kopetzki et al., Yeast 5 (1989) 11, at 405 nm and 30° C. with 2 mM para-nitrophenylglucopyranoside (PNPG) (Sigma) in 100 mM K$_2$HPO$_4$/KH$_2$PO$_4$ pH 6.8 as artificial substrate (Kopetzki et al., Yeast 5 (1989) 11).

III. Formation of a Disulfide Linked Chimeric Protein Mediated By Polyionic Fusion Peptides Association was performed in 20 mM Tris-HCl pH 7.5; 2 mM EDTA in the presence of a redox system. Oxidized and reduced glutathione were used at a molar ratio of 10:1 with an overall concentration of 2 mM (1.8 mM GSSG/0.2 mM GSH). The polypeptides were incubated in equimolar amounts (3 µmol/l) at 20° C. for 48 h. For analysis the reaction was stopped with iodoacetamide (final concentration 20 mM in Tris-HCl pH 8.0) and the samples were separated on a 12% SDS-PAGE under oxidizing and reducing conditions. Lanes containing Fab were detected by immunobloting on nitrocellulose.

Alternatively reaction products were separated on a gel-filtration column (TSKgel 2000 SW$_{XL}$; TosoHaas) in a 50 mM Na$_2$HPO$_4$/NaH$_2$PO$_4$ buffer containing 300 mM NaCl at a flow rate of 0.75 ml/min using a Vision Workstation (BioCad Vision station; Perseptive Biosystems).

Figure 5:
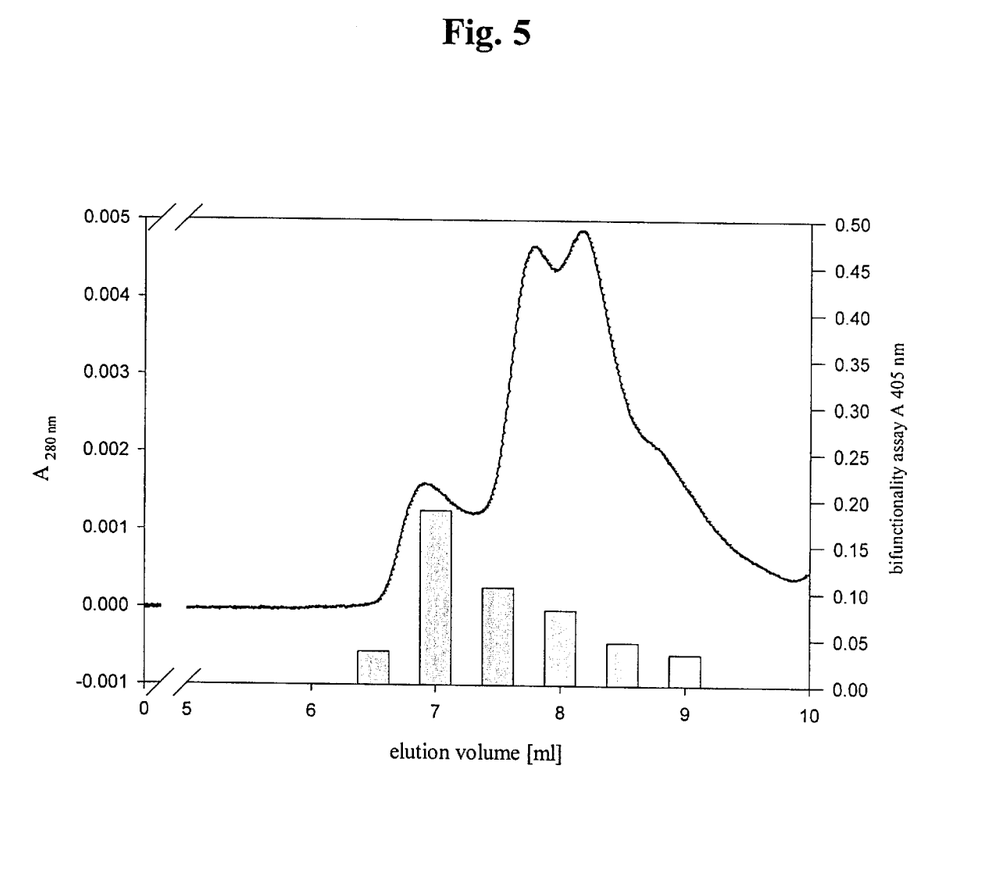

200 µl of the association reaction were injected into the column. Fractions were tested for antigen binding functionality, enzyme activity and bifunctionality. Bifunctionality was detected with a modified ELISA system: incubation in the presence of biotinylated creatinekinase at room temperature for one hour in streptavidin coated tubes (Roche Diagnostics GmbH), followed by washing twice with high salt buffer (2M NaCl; 10 mM Tris-HCl; pH 7.5) and once with low salt buffer (10 mM Tris-HCl; pH 7.5) and detection at 405 nm after 3 hours incubtion with 2 mM pNPG in 100 mM K$_2$HPO$_4$/KH$_2$PO$_4$; pH 6.8 at 30° C. Association reactions were performed in the absence and in the presence of 500 mM NaCl. The association of the single species was also investigated at low and high ionic strength. As a control FabD$_{10}$SCP was incubated with α-glucosidase wild-type protein.

The single species incubated alone did not react to a higher molecular product neither at low nor at high ionic strength. Further FabD$_{10}$SCP did not react with wildtype α-glucosidase. The reaction of FabD$_{10}$SCP with a-glucosidaseR$_{10}$CGP in the absence of NaCl was the only one leading to a product with bifunctional activity.

Example 3

Specific Association Between Virus Like Particles (VLP's) and an Antibody Fragment, Mediated By Polyionic Interactions The covalent association of VLP's of polyoma coat-protein VP1 and disulfide bridged Fv-fragments (ds Fv) of mAb B3, based on engineered polyionic peptide sequences, is another example for the present invention. The invention includes the production of VLP's, the production of ds Fv-fragments and the following association.

I) Production of VLP's a) Insertion of a polyionic peptide in VP1 on cDNA-level and expression in E. coli b) Purification of the soluble (mutant) protein VP1-Glu c) in vitro assembly of VP1-Glu to VLP's II) Production of ds Fv a) Expression of ds Fv with a polyionic peptide sequence in E.coli b) Isolation of inclusion bodies (ib's) and solubilisation c) Renaturation and purification of ds Fv mAb B3

III) Association of VLP's With ds Fv's Mediated By Polyionic Interactions and Formation of a Intermolecular Disulfide Bridge I) Production of VLP's a) Insertion of a Polyionic Peptide Into VP1: Plasmid Construction and Expression in E. coli The polyoma coat protein VP1 is capable of assembling in vitro into icoasaedric VLP's (Salunke, D. M., et al. Cell 46 (1986) 895–904; Salunke, D. M., et al., Biophysical J. 56 (1989) 887–904). The plasmid pALVP1TAC (Leavitt, A. D., et al., J. Biol. Chem. 260 (1985) 12803–12809) encodes the wildtype protein and allows the recombinant production of soluble pentameric protein in E.coli. Based on this plasmid a polyionic sequence was inserted in the solvent-exposed HI-loop on the surface of VP1 (Stehle, T., et al., Structure 4 (1996) 165–182). This sequence consists of 8 glutamates and one cysteine. For cloning of the mutant VP1 the sequence GluGluGluGluGluGluGluGluCys (E$_8$C, SEQ ID NO:10) was inserted between the amino acids Asn$^{294}$ and Tyr$^{295}$ on cDNA-level by QuickChange™ site directed mutagenesis kit (Stratagene).

For expression the resulting plasmid encoding VP1-Glu was transformed into Eco B. The expression strain was cultivated on mineral salt medium at 30° C. at a scale of 5 liters in a Biostat-Fermenter (Braun) using the fed-batch technique. The recombinant expression of VP1-Glu was induced by 0.4 mM IPTG at a cell density of OD$_{600}$=20. Six hours after induction the cells were harvested by centrifugation (8000 g, 15 min) and stored at −70° C.

b) Purification of the Mutant Soluble Protein

For preparation of mutant VP1-Glu 50 g cells were resuspended in 500 ml buffer A (50 mM Tris HCl; pH 7.4; 5% glycerol; 2 mM EDTA; 200 mM NaCl; 4 mM DTT). Cell lysis was performed by high pressure dispersion (Gaulin, 1200 bar) in presence of 1 unit/ml Benzonase, 20 µg/ml RNase and 4 tablets of complete protease inhibitor coctail (Roche Diagnostics GmbH, DE). The lysate was centifuged for 30 min at 47,000 g.

The first purification and concentration step consists of a fractionated ammonium sulphateprecipitation between 17.5% and 27.5% saturation of salt. The resuspended protein was loaded on an anion exchange column (Poros 20 HQ). In a linear gradient ranging from 200 mM to 1M NaCl in buffer A about 30 column volumes VP1-Glu eluted at 500 mM NaCl as almost homogeneous protein. Afterwards the eluate was incubated at 20° C. for 20 min with 2.5 units/ml Benzonase and 20 µg/ml RNase in the presence of 10 mM magnesium chloride. Subsequently a size exclusion chromatography (Pharmacia Superdex 200 prep grade, in Puffer A) was performed to separate the pentameric VP1 from higher oligomeric and aggregated material.

c) In vitro Assembly of VP1-Glu (Empty Virus Like Particles—VLP's)

For assembly to VLP's the purified pentameric VP1-Glu was dialyzed against buffer B (20 mM Tris, pH 7.4; 0.75 M ammonium sulphate; 5% glycerol; 1 mM CaCl2) for 2 day at 15° C. Under these conditions the formation of VLP's is induced. In order to remove the ammonium sulphate the solution of VLP's was dialyzed against buffer C (20 mM Tris, pH 7.4; 200 mM NaCl; 5 % glycerin; 1 mM CaCl2) for 1 day at 15° C. and afterwards stored at 4° C. or −20° C.

II) Production of ds Fv a) Expression of ds Fv With a Polyionic Peptide Sequence in E.coli Based on the vector pUli 39-1, which encodes the cDNA of the VL domain coupled to pseudomonas exotoxin, and the vector pYR 38-2, encoding the VH domain (Reiter, Y., et al., Protein Engng. 12 (1995) 1323–1331), a disulfide stabilized Fv-Fragment with a polyionic fusion peptide was constructed. For this purpose a stop codon was introduced between the coding sequence of VL and the toxin part, thus creating an expression vector for the VL domain of mAb B3.

The $V_H$ domain, encoded on the plasmid pYR 38-2 was extended by a polyionic sequence ArgArgArgArgArgArgArgArgCysPro ($R_8CP$, SEQ ID NO:1) at the C-terminus. This extension was achieved by a two-step procedure using the QuickChange™ site directed mutagenenesis kit (Stratagene). First a oligonucleotide coding ArgArgArgArg-CysPro was inserted at the 3' end of the $V_H$ gene (Reiter, Y., et al., Protein Engng. 12 (1995) 1323–1331).

To complete the tag containing the R8CP peptide four more arginine were inserted by a second mutagnesis.

b) Isolation of ib's and Solubilisation of ib's

The $V_H$- and $V_L$-domain were separately expressed in E. coli as inclusion bodies. The preparation of ib's was performed according the method by Rudolph et al. (Rudolph et al., Folding Proteins, In: T. E. Creighton (ed.): Protein function: A Practical Approach, 57 (1996)). The ib's were stored at −70° C. Solubilisation of ib's were likewise performed according the method by Rudolph et al. (Rudolph et al., Folding Proteins, In: T. E. Creighton (ed.): Protein function: A Practical Approach, 57 (1996)).

c) Renaturation and Purification of ds Fv mAb B3

The ds Fv mAb B3 was renaturated by simultaneous dilution of solubilized $V_H$- und $V_L$-ib's in the folding buffer (100 mM Tris, pH 8.5; 1 mM EDTA; 0.5 M arginine; 1 mM GSH; 1 mM GSSG). Renaturation was performed at a total protein concentration of 30 μg/ml with a molar ratio of $V_H:V_L=5:1$. The renaturation mixture wase incubated at 10° C. for 7 days. Afterwards aggregated material was removed by centrifugation at 47,000 g for 30 min. In the case of correct folded protein an intermolecular disulfide bridge between $V_H$ and $V_L$ was formed. The soluble renaturate was concentrated by tangential flow (Vario-3-System Filtron; Minisette FSQ; cut off: 8 kDa) and the buffer was changed to buffer D (50 mM Tris, pH 7.5; 200 mM NaCl).

The polycationic sequence at the C-terminus of the $V_H$-domain allowed a purification of folded ds Fv by cation exchange chromatography. The renatured protein was loaded on a Poros20 HS column and eluted with a linear gradient from 0.2 to 1 M NaCl in buffer D. The ds Fv elutes as a homogeneous protein at 400 mM NaCl. The homogeneity of ds Fv was shown by gel filtration (Pharmacia Superdex 75), running with buffer D and SDS PAGE.

III) Covalent Association of VLP's With ds Fv's

Figure 4:
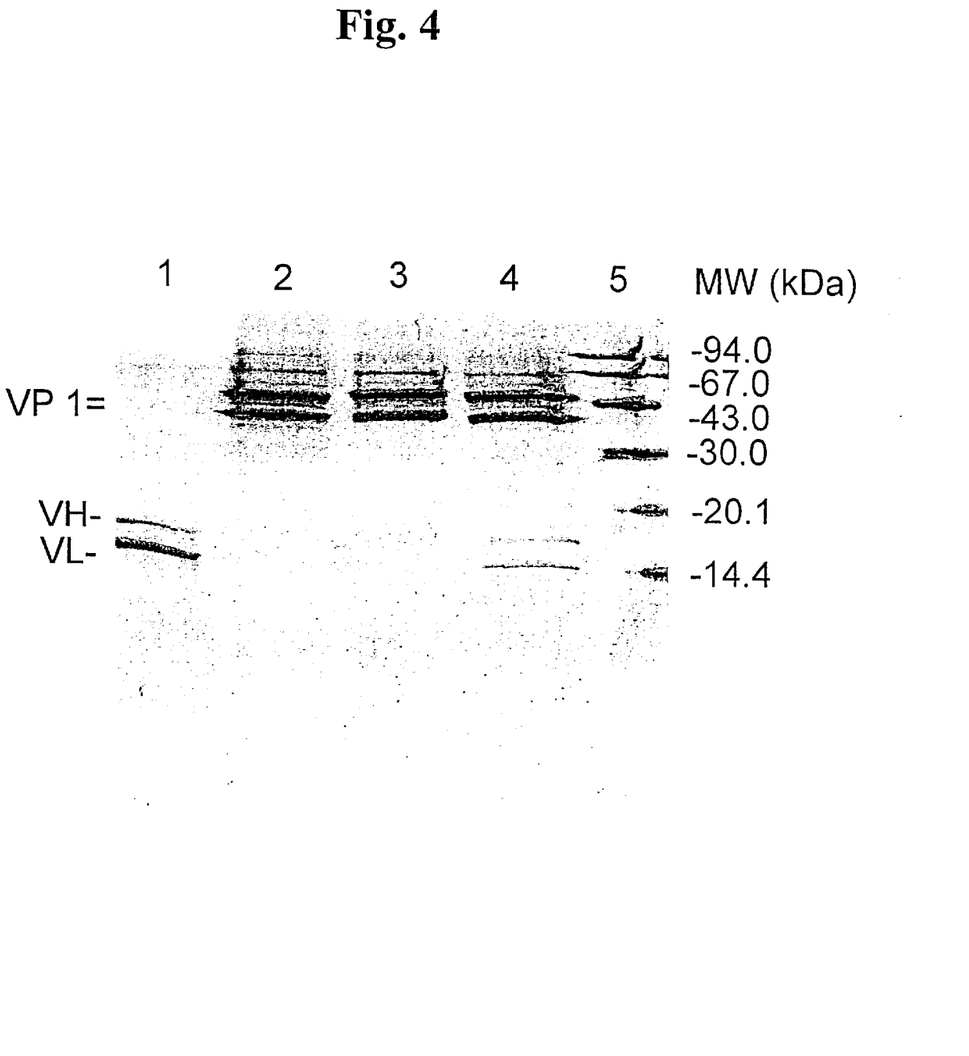
FIG. 4: Coomassie-stained SDS-PAGE (18%) under reducing conditions for evidence of directed associaton of VLP's with ds Fv's; Lanes : (1) dsFv dissociated in VH and VL; (2) association reaction between wildtype VLP's and ds Fv in the presence of 200 mM NaCl; (3) association reaction between VLP's build up by VP1-Glu and ds Fv in the presence of 750 mM ammonium sulphate; (4) association reaction between VLP's build up by VP1-Glu and ds Fv in the presence of 200 mM NaCl; (5) molecular weight marker

The directed association of ds Fv and VLP's was performed in buffer E (20 mM Tris; pH 7.4; 5% glycerol; 1 mM $CaCl_2$; 37.5 μM GSSG). The concentration of VP1-Glu used was 5 μM and the concentration of ds Fv 2.5 μM. The reaction was performed in the presence of 0.2 M NaCl and 0.75 M ammonium sulphate, respectively. As control, wild-type VP1 without polyionic sequence was mixed with ds Fv in the presence of 0.2 M NaCl. The reaction mixtures were incubated for 8 h at 20° C. and then applied on a gel filtration column (TosoHAAS TSK-Gel PW 6000 XL), equilibrated in buffer E and 0.2 M NaCl. Fractions containing VLP's were precipitated with sodium desoxycholate and analyzed by 18% SDS PAGE (FIG. 4) and Western Blot.

Only in the mixture with 0.2 M NaCl present and both polyionic proteins VP1-Glu and dsFv B3, respectively, a disulfide bridge between dsFv and mutant VLP's was formed, promoted by polyionic interactions between the polyionic fusion peptides. In presence of 0.75 M ammonium sulphate the polyionic interactions were suppressed and no disulfide was formed. Likewise, in the control mixture, no intermolecular disulfide bridges between dsFv and wildtype VLP's are detectable. These data indicate that polyionic fusion peptides induce heterodimerisation of proteins. In the given example, one of the reaction partners, VP1-Glu, stays in a multimeric form, allowing not only the coupling of one other functional protein but docking of several different polyionic tagged proteins is possible.

What is claimed is:

1. A method for producing a chimeric polypeptide having two polypeptide chains that are linked to each other by 1 to 3 cysteine-based disulfide bridges, which comprises:

(a) providing a first polypeptide chain that consists essentially of from 1 to 3 cysteines and from 4 to 12 basic amino acids selected from the group consisting of arginine, lysine, and ornithine, the first polypeptide having attached to its C- or N-terminus a first biologically active compound;

(b) providing a second polypeptide chain that consists essentially of 1 to 3 cysteines and 4 to 12 acidic amino acids selected from the group consisting of glutamate and aspartate, the second polypeptide having attached to its C- or N-terminus a second biologically active compound;

(c) bringing the first polypeptide chain into spacial proximity with the second polypeptide chain under conditions such that the basic amino acids on the first polypeptide chain interact ionically with the acidic amino acids on the second polypeptide chain; and (d) treating the first polypeptide chain and the second polypeptide chain that have interacted ionically with each other with an oxidizing agent under conditions such that the 1 to 3 cysteines of the the first polypeptide chain form disulfide bridges with the 1 to 3 cysteines of the second polypeptide chain to produce the chimeric polypeptide.

2. The method of claim 1 further comprising isolating the chimeric polypeptide.

3. The method of claim 1, wherein the biologically active compound attached to the first polypeptide chain differs from the biologically active compound attached to the second polypeptide chain.

4. The method of claim 1, wherein the biologically active compound is selected from the group consisting of antibodies, antibody fragments, and enzymes.

5. The method of claim 1, wherein the biologically active compound is a carbohydrate.

6. The method of claim 5, wherein the biologically active compound is a carbohydrate selected from the group consisting of monosaccharides, oligosaccharides, and polysaccharides.

7. The method of claim 1, wherein the biologically active compound is a peptide or protein.

8. The method of claim 7, wherein the biologically active compound is a peptide or protein selected from the group consisting of nucleoprotein, mucoprotein, lipoprotein, synthetic polypeptide, synthetic protein, or glycoprotein.

9. The method of claim 1, wherein the biologically active compound is a nucleic acid.

10. The method of claim 9, wherein the nucleic acid is selected from the group consisting of DNA and RNA.

11. The method of claim 1, wherein the first polypeptide chain and the second polypeptide chain each have 2 or 3 cysteines.

12. The method of claim 11, wherein the distance between any two cysteines in a polypeptide chain is more than one amino acid.

13. The method of claim 12, wherein the distance between any two cysteines in a polypeptide chain is from 3 to 6 amino acids.

14. The method of claim 1, wherein the biologically active compound attached to the first polypeptide chain is attached at the C-terminus and the biologically active compound attached to the second polypeptide chain is attached at the C-terminus.

15. The method of claim 1, wherein the biologically active compound attached to the first polypeptide chain is attached at the N-terminus and the biologically active compound attached to the second polypeptide chain is attached at the N-terminus.

16. The method of claim 1, wherein the biologically active compound attached to the first polypeptide chain is attached at the N-terminus and the biologically active compound attached to the second polypeptide chain is attached at the C-terminus.

17. The method of claim 1, wherein the biologically active compound attached to the first polypeptide chain is attached at the C-terminus and the biologically active compound attached to the second polypeptide chain is attached at the N-terminus.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:peptide ACE8

<400> SEQUENCE: 1

Ala Cys Glu Glu Glu Glu Glu Glu Glu Glu
  1               5                  10

<210> SEQ ID NO 2
<211> LENGTH: 10
<212> TYPE: PRT
<213> ORGANISM: Artificial Sequence
<220> FEATURE:
```

<223> OTHER INFORMATION: Description of Artificial Sequence:peptide ACK8

<400> SEQUENCE: 2

Ala Cys Lys Lys Lys Lys Lys Lys Lys
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:laminin
      nona-peptide

<400> SEQUENCE: 3

Cys Asp Pro Gly Tyr Ile Gly Ser Arg
 1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:peptide
                        D10SCP

<400> SEQUENCE: 4

Asp Asp Asp Asp Asp Asp Asp Asp Asp Asp Ser Cys Pro
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:peptide
                        R10CGP

<400> SEQUENCE: 5

Arg Arg Arg Arg Arg Arg Arg Arg Arg Arg Cys Gly Pro
 1               5                  10

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:primer NdeI
                        Fd

<400> SEQUENCE: 6
gcgttagcca tatgaccatg attacgaatt cccgg                              35

<210> SEQ ID NO 7
<211> LENGTH: 78
<212> TYPE: DNA
<213> ORGANISM: Artificial Sequence
<220> FEATURE:
<223> OTHER INFORMATION: Description of Artificial Sequence:primer
                        fdD10SCP

<400> SEQUENCE: 7
catagtccca agcttttacg ggcaagaatc atcgtcatca tcatcgtcgt catcatcacc   60
acaatccctg ggcacaat                                                78

<210> SEQ ID NO 8

```
<211> LENGTH: 31
<212> TYPE: DNA
<213> ORGANISM: Artificial Sequence
<220> FEATURE:
<223> OTHER INFORMATION: Description of Artificial Sequence:primer
      EcoRI1600

<400> SEQUENCE: 8 ataagagta cggagacaag acgctgtttg c                                31

<210> SEQ ID NO 9
<211> LENGTH: 76
<212> TYPE: DNA
<213> ORGANISM: Artificial Sequence
<220> FEATURE:
<223> OTHER INFORMATION: Description of Artificial Sequence:primer
                        R10CGP

<400> SEQUENCE: 9
aaacagaagc ttattatggt ccacatcgac gtcgacgacg ccggcgacgt cggcgtttga    60
ccaggtagat tctacc                                                   76

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:peptide E8C

<400> SEQUENCE: 10

Glu Glu Glu Glu Glu Glu Glu Glu Cys
  1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:peptide R8CP

<400> SEQUENCE: 11

Arg Arg Arg Arg Arg Arg Arg Arg Cys Pro
  1               5                  10
```